(12) United States Patent
Shyu et al.

(10) Patent No.: US 8,537,213 B2
(45) Date of Patent: Sep. 17, 2013

(54) METHOD FOR MEASURING VIA BOTTOM PROFILE

(75) Inventors: Deh-Ming Shyu, Miaoli County (TW); Yi-Sha Ku, Hsinchu (TW); Wei-Te Hsu, Taipei County (TW)

(73) Assignee: Industrial Technology Research Institute, Hsinchu (TW)

( * ) Notice: Subject to any disclaimer, the term of this patent is extended or adjusted under 35 U.S.C. 154(b) by 364 days.

(21) Appl. No.: 12/979,353

(22) Filed: Dec. 28, 2010

(65) Prior Publication Data

US 2012/0147171 A1    Jun. 14, 2012

(30) Foreign Application Priority Data

Dec. 8, 2010   (TW) ............................... 99142827 A

(51) Int. Cl.
*H04N 7/18*    (2006.01)
*G01B 11/02*   (2006.01)
*G01B 11/00*   (2006.01)
*G01B 9/02*    (2006.01)

(52) U.S. Cl.
USPC ............. 348/79; 356/496; 356/626; 356/485; 356/489

(58) Field of Classification Search
None
See application file for complete search history.

(56) References Cited

U.S. PATENT DOCUMENTS

| | | | |
|---|---|---|---|
| 5,905,575 A * | 5/1999 | Matsuoka | 356/496 |
| 5,966,204 A * | 10/1999 | Abe | 356/51 |
| 6,882,436 B2 | 4/2005 | Belk et al. | |
| 7,738,113 B1 * | 6/2010 | Marx et al. | 356/496 |
| 2006/0109483 A1 * | 5/2006 | Marx et al. | 356/609 |
| 2008/0030715 A1 * | 2/2008 | Kondo et al. | 356/73 |
| 2008/0049214 A1 * | 2/2008 | Maznev et al. | 356/51 |

* cited by examiner

*Primary Examiner* — Joseph Ustaris
*Assistant Examiner* — Ellyar Y Barazesh
(74) *Attorney, Agent, or Firm* — Jianq Chyun IP Office

(57) ABSTRACT

A method for measuring a via bottom profile is disclosed for obtaining a profile of a bottom of a via in a front side of a substrate. In this method, an infrared (IR) light source is transmitted from the back of the substrate to the bottom of the via through an objective by using an IR-microscope, and lights scattered from the bottom of the via are acquired by an image capturing device to generate an image, where the image displays a diameter ($2E_a$) of the via bottom profile and a diameter ($2E_c$) of a maximum receivable base area of the via for the IR-microscope. Thereafter, by using an elliptic equation, a minor axis radius thereof ($E_b$) is obtained, and thus the via bottom profile is obtained from a radius ($E_a$) of the via bottom profile and the minor axis radius ($E_b$) of the elliptic equation.

6 Claims, 5 Drawing Sheets

# METHOD FOR MEASURING VIA BOTTOM PROFILE

CROSS-REFERENCE TO RELATED APPLICATION

This application claims the priority benefit of Taiwan application serial no. 99142827, filed on Dec. 8, 2010. The entirety of the above-mentioned patent application is hereby incorporated by reference herein and made a part of this specification.

BACKGROUND OF THE INVENTION

1. Technical Field

The disclosure relates to a method for measuring a via bottom profile.

2. Background

Conventionally, a chip is fabricated in a two-dimensional (2D) space, though as complexity of the chip increases, horizontal area thereof in the 2D space is increased, so that the Moore's Law cannot be continually effective. Therefore, different chips are considered to be stacked for integration, so that three-dimensional (3D) chips are generated. By using a through-silicon via (TSV) package technique, the vertically stacked chips are electrically connected, so that a fabrication quality of the TSV and a measurement accuracy thereof may obviously influence a yield of the chip. However, the TSV generally has a high aspect ratio, and a depth and a via bottom profile thereof cannot be directly measured through an optical microscope.

Therefore, it was suggested by utilizing a chromatic confocal sensor which operates in the near infrared (NIR) region of the spectrum to measure a depth of a via in a wafer, as disclosed by U.S. Pat. No. 7,738,113 B1. In this patent, the chromatic confocal sensor is used to measure from a bottom of the wafer, where a thickness of the wafer is first measured, i.e. a distance between the bottom and the top of the wafer, and then a distance between a bottom of the via and the bottom of the wafer is measured. Then, the depth of the via is obtained by subtracting the two distances.

However, a method for measuring a via bottom profile of the TSV is still not disclosed.

SUMMARY

A method for measuring a via bottom profile is introduced herein for obtaining a profile of a bottom of a via at a front side of a substrate. In this method, an infrared (IR) light source is incident from the back of the substrate to the bottom of the via through an objective by using an IR-microscope, and lights scattered from the bottom of the via are acquired by an image capturing device to generate an image, where the image displays a diameter ($2E_a$) of the via bottom profile and a diameter ($2E_c$) of a maximum receivable base area of the via for the IR-microscope. Thereafter, by using an elliptic equation, a minor axis radius thereof ($E_b$) is obtained, and thus the via bottom profile is obtained from a radius ($E_a$) of the via bottom profile and the minor axis radius ($E_b$) of the elliptic equation.

In order to make the aforementioned and other features and advantages of the disclosure comprehensible, several exemplary embodiments accompanied with figures are described in detail below.

BRIEF DESCRIPTION OF THE DRAWINGS

The accompanying drawings are included to provide a further understanding of the disclosure, and are incorporated in and constitute a part of this specification. The drawings illustrate embodiments of the disclosure and, together with the description, serve to explain the principles of the disclosure.

DETAILED DESCRIPTION OF DISCLOSED EMBODIMENTS

Figure 1:
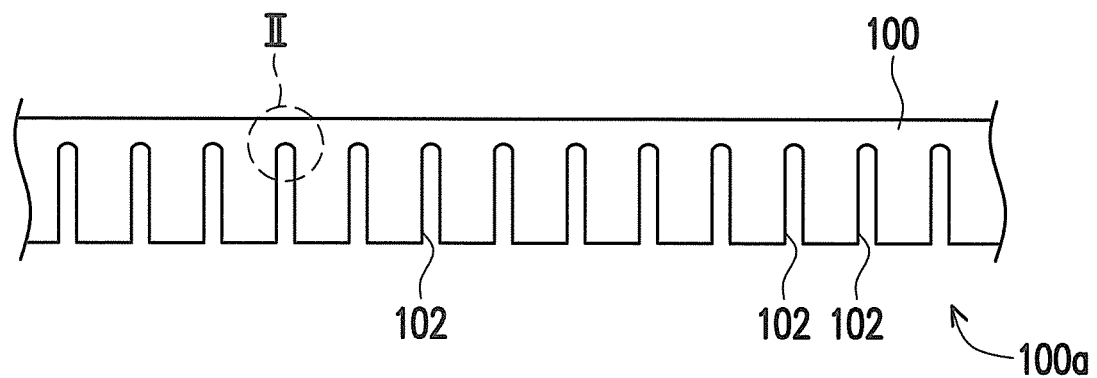
FIG. 1 is cross-sectional view of vias of a front side of a substrate.
Figure 2:
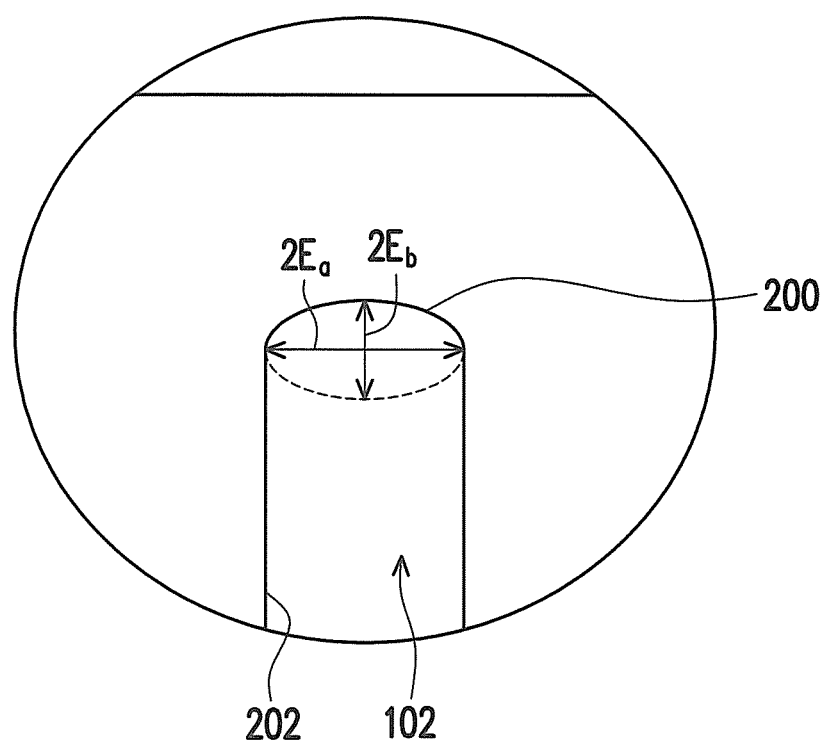
FIG. 2 is an enlarged diagram of a part II of FIG. 1

FIG. 1 is a diagram illustrating a plurality of vias 102 disposed on a front side 100a of a substrate 100, and an enlarged diagram of a part II is shown in FIG. 2. In FIG. 2, the via 102 includes a bottom 200 and a sidewall 202. A profile of the bottom 200 of the via 102 can be represented by an elliptic equation (1):

$$\frac{x^2}{E_a^2} + \frac{z^2}{E_b^2} = 1 \qquad (1)$$

Where, $E_a$ and $E_b$ are respectively a major axis radius and a minor axis radius of the elliptic equation (1).

In order to accurately obtain the profile of the bottom 200 of the via 102 of FIG. 2, values of $E_a$ and $E_b$ have to be obtained. Therefore, a method of measuring a via bottom profile is provided below.

Figure 3:
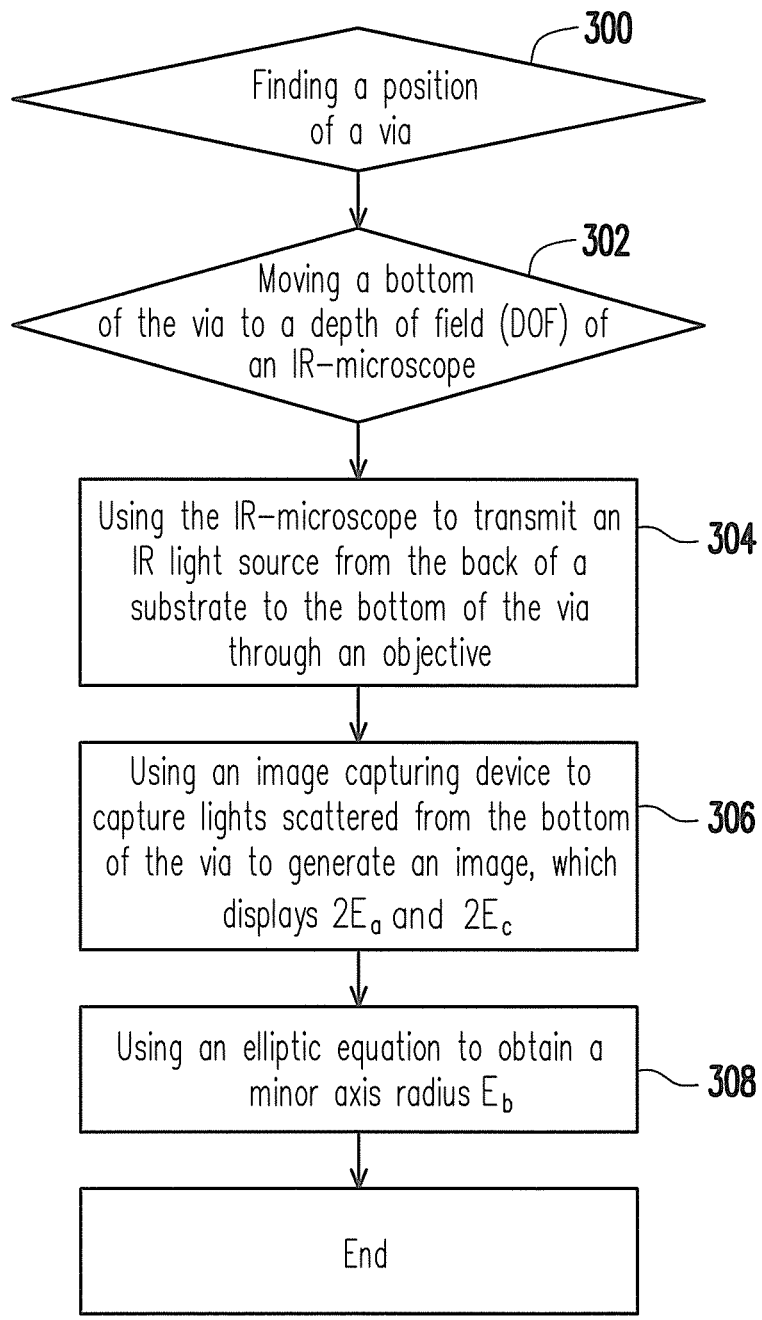
FIG. 3 is a flowchart illustrating steps for measuring a via bottom profile according to an exemplary embodiment.

FIG. 3 is a flowchart illustrating a method for measuring a via bottom profile according to an exemplary embodiment. The method of FIG. 3 can be performed in collaboration with a suitable equipment, for example, an optical system of FIG. 4.

Referring to FIG. 3, before the measurement, a position of a via is first found (step 300). In order to find the position of the via, an infrared (IR)-microscope 400 of FIG. 4 can be utilized to find the via 102 in the substrate 100. Then, a step 302 is executed, by which the bottom of the via is moved to a depth of field (DOF) of the IR-microscope 400.

Figure 4:
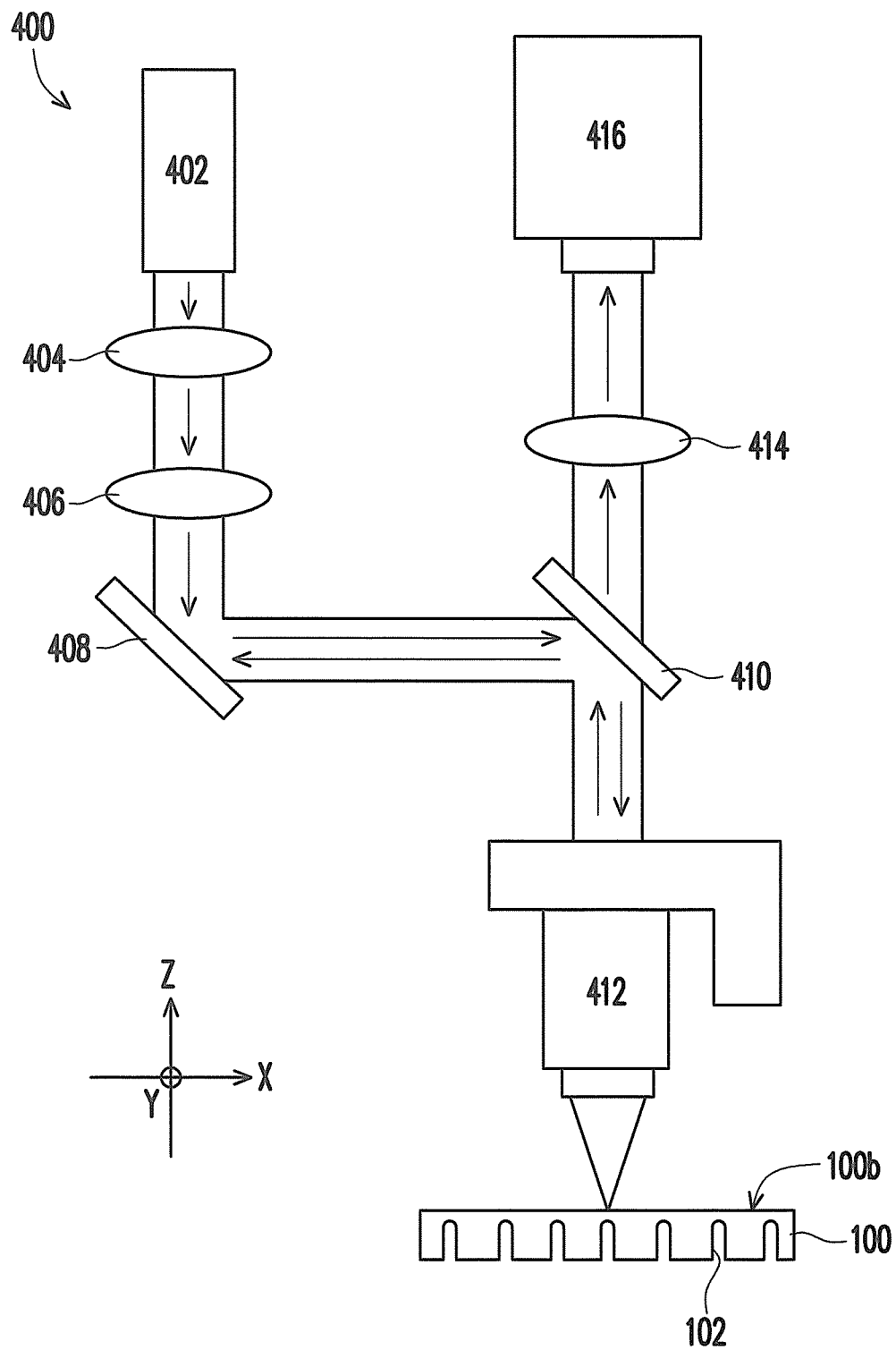
FIG. 4 is a schematic diagram of an optical system used for executing measurement steps of FIG. 3 according to an exemplary embodiment.

Then, in step 304, an IR light source is transmitted from the back of the substrate to the bottom of the via through an objective by using the IR-microscope, and such step can be implemented through the IR-microscope 400 of FIG. 4. In FIG. 4, an IR light source 402 is incident to an objective 412 through illumination lenses 404 and 406, a reflection mirror 408 and a semi reflection mirror 410, where a wavelength range of the IR light source 402 is, for example, 1000 nm-1500 nm. Moreover, when the substrate 100 is a silicon wafer, the objective 412 can be a silicon corrected lens. Then, the light source emitted from the objective 412 is incident to the bottom of the via 102 from a back 100b of the substrate 100.

Figure 5:
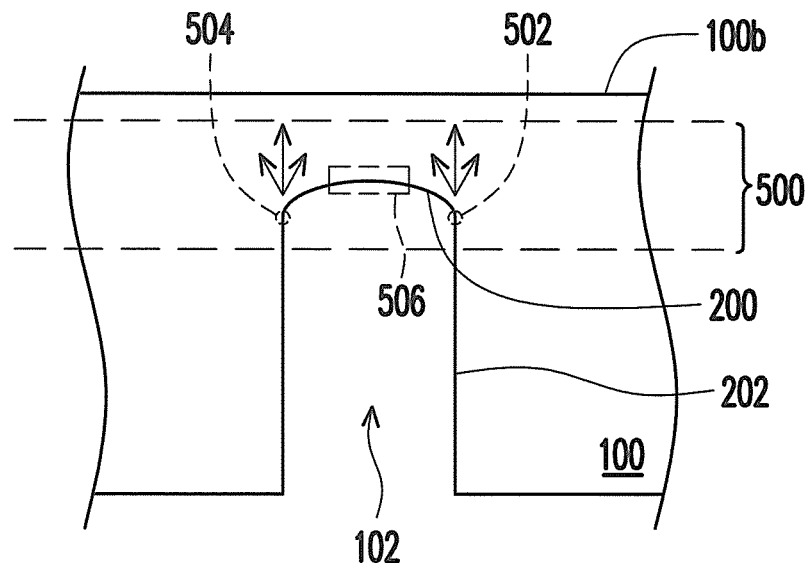
FIG. 5 is an enlarged diagram of a via in a substrate of FIG. 4.

When the IR light source 402 is incident to the bottom of the via 102, referring to an enlarged diagram of the via 102 of FIG. 5, since a profile of the bottom 200 of the via 102 is located in the DOF 500 of the IR-microscope 400, lights scattered from the bottom 200 are returned back to the objective 412. Due to a light receiving limitation of the IR-microscope 400, the light is received only when a scattered angle thereof is within a receivable angle of the objective 412, for example, lights (indicated by arrows) scattered by boundaries 502 and 504 of the bottom 200 and the sidewall 202 of the via 102, and lights scattered by a central portion 506 of the bottom 200 of the via 102. In other words, when a slope of the bottom 200 of the via 102 is greater than the receivable angle of the objective 412, the corresponding scattered light cannot enter the objective 412.

Figure 6:
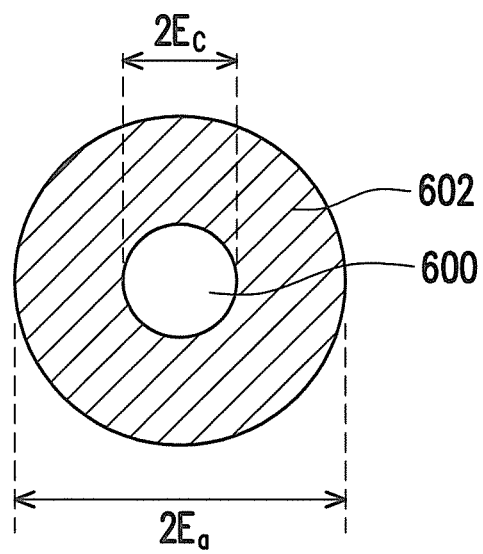
FIG. 6 is a schematic diagram of an image obtained through a step 306 of FIG. 3.

Thereafter, in step 306, an image capturing device is used to capture the lights scattered from the bottom of the via to generate an image. Referring to the IR-microscope 400 of FIG. 4, the light scattered by the via 102 is incident to an image capturing device 416 (for example, a charge-coupled device) through the objective 412 and a lens 414. The image obtained by the capturing device 416 can be further processed to strengthen a contrast thereof. FIG. 6 is a schematic diagram of an image obtained through the step 306.

In FIG. 6, a bright area 600 represents a central portion (referring to the central portion 506 of FIG. 5) of the via bottom, a dark area 602 represents an area of the via bottom with a slope greater than the receivable angle of the objective, so that it presents a dark image since no light is received. Compared to the enlarged diagram of the via 102 of FIG. 5, it is known that the dark area 602 is the boundary of the bottom and the sidewall of the via, so that a diagram of the dark area 602 is a diameter ($2E_a$) of the via bottom profile. The bright area 600 is a maximum receivable base area of the via for the IR-microscope 400, so that a diagram thereof is ($2E_c$).

Figure 7:
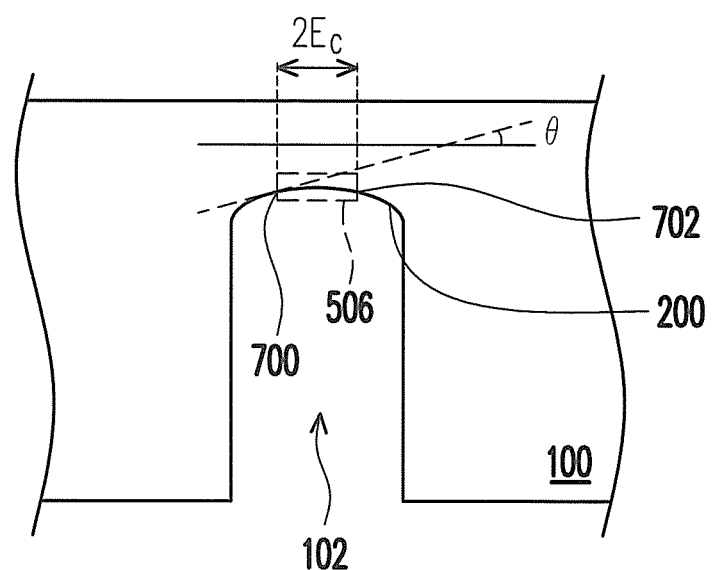
FIG. 7 is an enlarged diagram of a via in a substrate of FIG. 4.

FIG. 7 is a diagram illustrating a definition of the slope of the bottom 200 of the via 102, in which device symbols the same as that of FIG. 5 are used. According to FIG. 7, it is known that $2E_c$ is the diagram of the maximum receivable base area of the via for the IR-microscope, and boundaries thereof are 700 and 702. Based on the boundary 700, a slope M and an angle θ of the maximum receivable base area of the via can be obtained.

Then, referring to FIG. 3, by using the elliptic equation (1), the minor axis radius ($E_b$) is obtained, and thus the via bottom profile can be obtained from the radius ($E_a$) of the via bottom profile and the minor axis radius ($E_b$) of the elliptic equation. A method of using the elliptic equation (1) to obtain the minor axis radius is as follows.

First, a slope equation (2) is obtained according to the elliptic equation (1):

$$\frac{dz}{dx} = m = \frac{E_b^2 x}{E_a^2 \sqrt{E_b^2 - \left(\frac{E_b}{E_a}x\right)^2}} \quad (2)$$

Where, m is the slope of the elliptic equation (1), and when x is a radius ($E_c$) of the maximum receivable base area of the via for the IR-microscope, the slope is M, so that the minor axis radius $E_b$ of the elliptic equation (1) is a following equation (3):

$$E_b = \frac{M \cdot E_a \sqrt{E_a^2 - E_c^2}}{E_c} \quad (3)$$

Where, $E_a$ and $E_c$ can be directly obtained from the dark area 602 and the bright area 600 of the image of FIG. 6, and M is a fixed parameter of the IR-microscope, so that the value of $E_b$ of the equation (3) is figured. In this way, the profile of the bottom 200 of the via 102 of FIG. 2 is obtained.

An experiment is provided below to verify an effect of the method for measuring the via bottom profile of the disclosure.

Experiment: measurement of a bottom profile of a via formed by laser

First, a position of the via is found, and the position of the via bottom is moved to the DOF of an IR-microscope. Then, a CCD is used to obtained the image of FIG. 6. Meanwhile, an image processing is performed to strengthen a contrast of the image.

Then, values of $E_a$ and $E_c$ are obtained according to the image, which are respectively 16.55 μm and 5.84 μm, and the value M of the IR-microscope is 0.106. Finally, the value $E_b$ of 4.55 μm is obtained according to the equation (3).

In summary, in the disclosure, the IR-microscope (IR light source) and the image capturing device (CCD) are used in the optical system structure to obtain an image of the via bottom, and the obtained image is processed and calculated to accurately obtain the via bottom profile.

It will be apparent to those skilled in the art that various modifications and variations can be made to the structure of the disclosure without departing from the scope or spirit of the disclosure. In view of the foregoing, it is intended that the disclosure cover modifications and variations of this disclosure provided they fall within the scope of the following claims and their equivalents.

What is claimed is:

1. A method for measuring a via bottom profile, for obtaining a profile of a bottom of a via in a front side of a substrate, the method comprising:
   using an IR-microscope to transmit an infrared (IR) light source from a back of the substrate to the bottom of the via through an objective;
   using an image capturing device to capture lights scattered from the bottom of the via to generate an image, wherein the image displays a diameter ($2E_a$) of the via bottom profile and a diameter ($2E_c$) of a maximum receivable base area of the via for the IR-microscope; and
   using an elliptic equation to obtain a minor axis radius ($E_b$) of the elliptic equation, so that the via bottom profile is obtained from a radius ($E_a$) of the via bottom profile and the minor axis radius ($E_b$) of the elliptic equation, wherein
   the elliptic equation is represented by an equation (1):

$$\frac{x^2}{E_a^2} + \frac{z^2}{E_b^2} = 1 \quad (1)$$

in the equation (1), $E_a$ is the radius of the via bottom profile, and $E_b$ is the minor axis radius of the elliptic equation;
a slope equation (2) is obtained according to the equation (1):

$$\frac{dz}{dx} = m = \frac{E_b^2 x}{E_a^2 \sqrt{E_b^2 - \left(\frac{E_b}{E_a}x\right)^2}} \quad (2)$$

in the equation (2), m is the slope of the equation (1), and when x is a radius ($E_c$) of the maximum receivable base area of the via for the IR-microscope, the slope is M, so that the minor axis radius $E_b$ is represented by an equation (3):

$$E_b = \frac{M \cdot E_a \sqrt{E_a^2 - E_c^2}}{E_c} \quad (3)$$

in the equation (3), M is a fixed parameter of the IR-microscope.

2. The method for measuring the via bottom profile as claimed in claim 1, wherein the image capturing device comprises a charge-coupled device (CCD).

3. The method for measuring the via bottom profile as claimed in claim 1, wherein when the substrate is a silicon wafer, the objective is a silicon corrected objective.

4. The method for measuring the via bottom profile as claimed in claim 1, wherein a wavelength range of the IR light source is 1000 nm-1500 nm.

5. The method for measuring the via bottom profile as claimed in claim 1, wherein before the step of using the IR-microscope to transmit the IR light source from the back of the substrate to the bottom of the via through the objective, the method further comprises:

finding a position of the via; and moving the bottom of the via to a depth of field (DOF) of the IR-microscope.

6. The method for measuring the via bottom profile as claimed in claim 1, wherein the step of using the image capturing device to capture the lights scattered from the bottom of the via to generate the image comprises performing image processing to strengthen a contrast of the image.

* * * * *